US00PP34553P2

(12) United States Plant Patent
Shoup

(10) Patent No.: US PP34,553 P2
(45) Date of Patent: Sep. 13, 2022

(54) SHRUB ROSE PLANT NAMED 'VANILLA VIXEN'

(50) Latin Name: *Rosa hybrida*
Varietal Denomination: Vanilla Vixen

(71) Applicant: George Michael Shoup, Brenham, TX (US)

(72) Inventor: George Michael Shoup, Brenham, TX (US)

( * ) Notice: Subject to any disclaimer, the term of this patent is extended or adjusted under 35 U.S.C. 154(b) by 0 days.

(21) Appl. No.: 17/484,908

(22) Filed: Sep. 24, 2021

(51) Int. Cl.
*A01H 5/02* (2018.01)
*A01H 6/74* (2018.01)

(52) U.S. Cl.
USPC ..... Plt./104

(58) Field of Classification Search
USPC ..... Plt./101, 102, 104
See application file for complete search history.

*Primary Examiner* — Karen M Redden

(57) ABSTRACT

A new and distinct variety of shrub rose plant, herein referred to by its cultivar name, 'Vanilla Vixen', is provided which abundantly, substantially, and continuously forms yellow colored cupped rosette blooms. The new variety exhibits a unique vanilla fragrance, which is unusual for a rose. The growth habit is short, rounded and bushy. The foliage is smooth, with a slightly glossy finish. The plant propagates from cuttings easily, and uniformly. The new variety is well suited to growing as a container rose, pot rose, and as a source of attractive ornamentation and fragrance in the landscape.

1 Drawing Sheet

Botanical/commercial classification:
Latin name—*Rosa hybrida.*
Varietal denomination: 'Vanilla Vixen'.

SUMMARY OF THE INVENTION

The new variety of *Rosa hybrida* shrub rose plant was created at Brenham, Tex., U.S.A., by artificial pollination wherein two parents were crossed which previously had been observed in the hope that each would contribute their desired traits. The female parent (i.e., the seed parent) was a non-patented seedling derived from the self-pollination of the variety 'WEKcisbako' (U.S. Plant Pat. No. 18,552). The male parent (i.e., the pollen parent) was the 'Radcarn' variety (U.S. Plant Pat. No. 22,172). The parentage of the new variety can be summarized as follows:

Seedling of 'WEKcisbako' x 'Radcarn'

The seeds resulting from the above pollination were stratified in an artificial environment and sown into trays in a greenhouse environment. Seedlings were obtained and displayed phenotypic and biological variation. Selective trialing and evaluation of the seedlings resulted in the identification of a single plant of the new variety.

It was found that the new shrub rose plant of the present invention possesses the following combination of characteristics:

(a) abundantly, substantially, and continuously forms yellow colored cupped-rosette blooms,
(b) exhibits a short, bushy, and round growth habit,
(c) exhibits blooms with an unusual vanilla fragrance,
(d) exhibits a high bloom to foliage ratio when blossoming,
(e) forms disease resistant foliage with a smooth and slightly glossy finish, (f) is well suited for growing as container rose, pot rose, and as a source of attractive ornamentation and fragrance in the landscape.

The new variety can be readily distinguished from its ancestors upon inspecting the blossoms. More specifically, the 'Vanilla Vixen' variety forms dissimilar bright yellow blossoms, and the parental variety 'Radcarn' forms dissimilar rose-pink blossoms with a white reverse. Additionally, the new variety can be readily distinguished from its ancestors upon inspecting the bloom count, and bloom shape. 'Vanilla Vixen' forms cupped rosette blossoms with a very high petal count while the parental varieties Seedling of 'WEKcisbako' and 'Radcarn' form dissimilar flat semi-double, and ovoid whorled rosette blossoms respectively.

The new variety of the present invention also can be readily distinguished from other shrub rose plants, including the 'WEKvossutono' variety (U.S. Plant Pat. No. 18,473) upon inspection of the blossoms. More specifically, the 'Vanilla Vixen' variety forms approximately 20% more blooms when blossoming when compared to the 'WEKvossutono' variety.

Asexual reproduction of 'Vanilla Vixen' was done by taking cuttings in Brenham Tex., U.S.A. in beginning in 2019. Cuttings were taken from mature stems that were approximately 10 to 15 cm in length and approximately 0.75 cm in diameter. Initial cuttings were taken of the new variety and grew into mature plants. Subsequent cuttings were taken of the initial asexually reproduced plants and grown into mature plants. Mature plants of both the initially propagated plants and the subsequently propagated plants were compared. There was no observable difference between the generations. Therefore, it was demonstrated that the characteristics of 'Vanilla Vixen' remain stable, uniform and true to type in successive generations of asexual reproduction.

BRIEF DESCRIPTION OF THE DRAWING

The accompanying color illustration shows as true is as is reasonably possible to obtain in color photographs of this type, the typical characteristics of the plant parts, i.e., the flowers, buds, stems and leaves of the new rose, 'Vanilla Vixen'. The illustrated rose plant parts were approximately one year of age and were observed during August, while growing on their own roots in Brenham, Tex., U.S.A. Flowers, buds, and stem growth are displayed in various stages of maturity. The upper side and under side of the leaves, blooms and petals are displayed.

DETAILED BOTANICAL DESCRIPTION

The chart used in the identification of colors is The Royal Horticultural Society Colour Chart (R.H.S. Colour Chart) Edition V. The description is based one year old specimens of the new variety during August while growing outdoors on their own roots at Brenham, Tex., U.S.A.

Class: Shrub Rose. Cultivar 'Vanilla Vixen'.

Plant:

*Height*.—Approximately 0.5 m on average at maturity.

*Width*.—Approximately 0.45 m on average at maturity.

*Habit*.—Erect, and stout.

Stems:

*Size*.—Approximately 41 cm tall by 0.7 cm in caliper.

*Color*.—Immature: Turquoise-Green Group N144A. Mature: Turquoise-Green Group 144A.

*Prickles*.—Size: Approximately 1.2 cm in length on average. Quantity: Average. Color: Turquoise-Green Group 151A. Shape: Declining. Density: Average.

*Texture*.—Smooth.

*Internodal spacing*.—Approximately 4.4 cm on average.

Leaves:

*Arrangement*.—Alternate, odd-pinnate, and compound.

*Margin*.—Doubly serrate.

*Stipules*.—Size: Approximately 0.9 cm×0.5 cm on average. Margin: Adnate, recurved, and gland-ciliate edges. Color: Turquoise-Green Group 144A. Texture: Smooth.

*Size*.—Approximately 10 cm×7 cm on average.

*Petioles*.—Color upper surface: Turquoise-Green Group 152A. Color under surface: Turquoise-Green Group N144A. Size: Approximately 5 cm×0.8 mm on average. Shape: Filiform.

*Rachis*.—Color: Turquoise-Green Group N144A.

*Leaflets*.—Number: 5 and 7. Shape: Ovate. Size: Approximately 3.25 cm×2.5 cm on average. Venation: Reticulate. Venation Color: Turquoise-Green Group 152A. Apex: Subacuminate. Base: Acute. Texture Upper Surface: Smooth, slightly waxy. Texture Under Surface: Matte. Overall Appearance: Light green, smooth, and semi-glossy. Color (Young Foliage) Upper Surface: Turquoise-Green Group 152B. Color (Young Foliage) Under Surface: Brown-Grey Group 175A to 175B. Color (Adult Foliage) Upper Surface: Turquoise-Green Group 144A. Color (Adult Foliage) Under Surface: Turquoise-Green Group 152A.

Inflorescence:

*Average size of inflorescence*.—Approximately 9 cm×7 cm on average.

*Number of flowers per inflorescence*.—Approximately 3 to 5 on average.

*Florescence type*.—Intermediate between corymbose to paniculate.

*Peduncle*.—Color: Turquoise-Green Group N144C. Length: Approximately 5.75 cm on average. Diameter: Approximately 2.5 mm on average. Texture: Gland-ciliate.

*Sepals*.—Number: 5. Size: Approximately 2 cm×0.8 mm on average. Arrangement: Pentamerous and imbricate. Shape: Obcuneate. Margin: Laciniate. Apex: Foliaceous. Base: Truncate. Texture: Pubescent. Color Upper Surface: Turquoise-Green Group 144C. Color Under Surface: Turquoise-Green Group 144C.

*Buds*.—Shape: Globose. Size: Approximately 1.3 cm to 1 cm on average. Color (When Opening) Inner Surface: Yellow-Red Group 6A. Color (When Opening) Outer Surface: Yellow-Red Group 11B.

Flower:

*Form*.—Cupped rosette.

*Diameter*.—Approximately 6.5 cm on average.

*Color*.—(When Opening) Upper Surface: Yellow-Red Group 6A. (When Opening) Under Surface: Yellow-Red Group 11B. (When Blooming) Upper Surface: Yellow-Red Group 6A. (When Blooming) Under Surface: Yellow-Red Group 11B. (End Of Blooming) Upper Surface: Yellow-Red Group 11C. (End Of Blooming) Under Surface: Yellow-Red Group 11C.

*Fragrance*.—Vanilla.

*Petal form*.—Cuneate-mucronate.

*Petals*.—Size: Approximately 2.8 cm×2.2 cm on average. Margins: Entire. Apex: Mucronate. Base: Acute. Texture: Smooth. Number: Approximately 160 on average, of which 50% are petaloids. Petaloids: Number (80); are approximately 50% of the size of petals and are the exact same color as the petals. Petal Drop: Easily and cleanly after blooming.

*Stamen number*.—Approximately 40 on average.

*Anther color*.—Yellow-Red Group 10A.

*Anther shape*.—Oval to oblong.

*Anther length*.—Approximately 1.5 mm on average.

*Filament color*.—Yellow-Red Group 9A.

*Filament length*.—Approximately 5 mm on average.

*Pollen quantity*.—Average amount of pollen produced.

*Pollen color*.—Yellow-Red Group 17A.

*Pistil form*.—Free and exerted.

*Pistil number*.—Approximately 120 on average.

*Stigma color*.—Yellow-Red Group 17A.

*Style color*.—Yellow-Red Group 10D.

*Style length*.—Approximately 7 mm on average.

*Receptacle*.—Oblate to spheroid. Achenes form on the inside of the fruit. Size: Approximately 1 cm×0.8 cm on average when mature.

*Rate of flower opening*.—Slow rate of flower opening.

*Lasting quality*.—On plant: Approximately 4 to 5 days on average. In vase: Unknown.

Development:

*Vegetation*.—Appears overall rounded and compact.

*Growth rate*.—Average rate of growth.

*Hip/seed formation*.—None unless manually pollenated.

Root system:

*Root color*.—Yellow-Red Group 19C.

*Root habit*.—Well rounded.

Physiology:

*Disease resistance*.—Above average resistance to black spot *Diplocarpon rosae*, downy mildew *Per-*

*onospora sparsa*, powdery mildew *Podosphaera pannosa*, and *Cercospora* leaf spot *Cercospora rosicola*.

*Cold hardiness*.—The variety has been found to be suitable for climactic conditions in USDA Plant Hardiness Zone 8. Based on the performance of its parent varieties, it is likely, although untested, that the new variety is also suitable for climatic conditions of USDA Plant Hardiness Zones 6 and 7.

*Heat tolerance*.—The new variety exhibits above average heat tolerance, as blooms do not reduce in size, when temperatures are in excess of 100° F., as compared to similar commercial variety 'WEKvossutono' which does reduce in size under the aforementioned conditions. The variety has been found to be suitable for climactic conditions in USDA Plant Hardiness Zone 8. Based on the performance of its recent ancestors, it is likely, although untested, that the new variety is also suitable for climatic conditions of USDA Plant Hardiness Zone 9.

*Drought tolerance*.—The new variety exhibits average drought tolerance.

I claim:

1. A new and distinct variety of shrub rose plant named 'Vanilla Vixen' characterized by the following combination of characteristics:

(a) abundantly, substantially, and continuously forms yellow colored cupped rosette blooms, (b) exhibits a short, bushy, and round growth habit, (c) exhibits blooms with an unusual vanilla fragrance, (d) exhibits a high bloom to foliage ratio when blossoming, (e) forms disease resistant foliage with a smooth and slightly glossy finish, and (f) is well suited for growing as container rose, pot rose, and as a source of attractive ornamentation and fragrance in the landscape, substantially as illustrated and described herein.

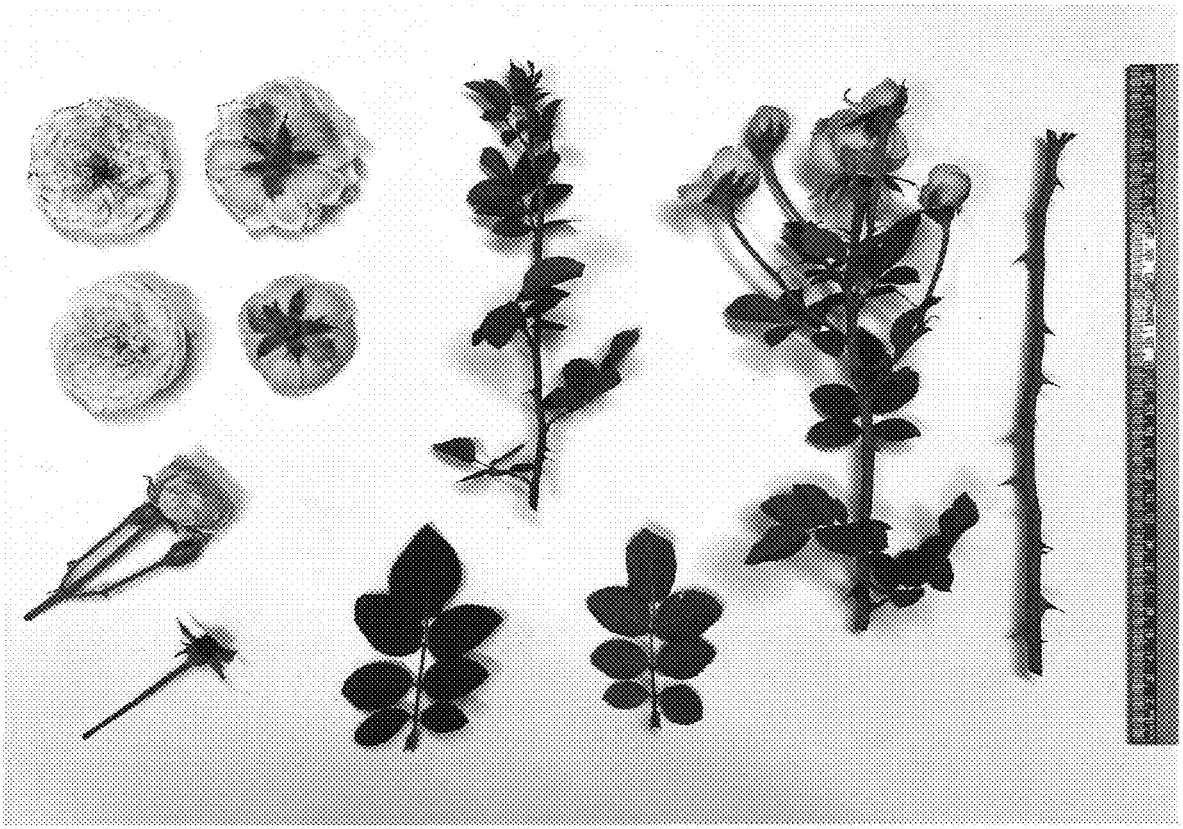

* * * * *